US010675177B2

(12) United States Patent
Vogel et al.

(10) Patent No.: US 10,675,177 B2
(45) Date of Patent: Jun. 9, 2020

(54) COOLING MAT COMPRISING EXPANDABLE ELEMENTS FOR COOLING A BODY OR BODY PART FOR MEDICAL OR PERFORMANCE-ENHANCING PURPOSES (COOL APP)

(71) Applicants: Friedrich Vogel, Baden (AT); Jakob Vogel, Baden (AT); Rudolf Faworka, Vienna (AT)

(72) Inventors: Friedrich Vogel, Baden (AT); Jakob Vogel, Baden (AT); Rudolf Faworka, Vienna (AT)

( * ) Notice: Subject to any disclaimer, the term of this patent is extended or adjusted under 35 U.S.C. 154(b) by 158 days.

(21) Appl. No.: 15/115,817

(22) PCT Filed: Jan. 26, 2015

(86) PCT No.: PCT/AT2015/000007
§ 371 (c)(1),
(2) Date: Aug. 1, 2016

(87) PCT Pub. No.: WO2015/113079
PCT Pub. Date: Aug. 6, 2015

(65) Prior Publication Data
US 2017/0007444 A1  Jan. 12, 2017

(30) Foreign Application Priority Data

Jan. 30, 2014  (AT) .................................... A68/2014

(51) Int. Cl.
*A61F 7/10* (2006.01)
*F25D 3/08* (2006.01)
*A61F 7/00* (2006.01)

(52) U.S. Cl.
CPC ................. *A61F 7/10* (2013.01); *F25D 3/08* (2013.01); *A61F 2007/0091* (2013.01);
(Continued)

(58) Field of Classification Search
CPC ............... A61F 7/10; A61F 2007/0091; A61F 2007/0095; A61F 2007/108; F25D 3/08; F25D 2303/0822; F25D 2331/8014
(Continued)

(56) References Cited

U.S. PATENT DOCUMENTS

| 1,941,173 A | 12/1933 | Lark-Horovitz |
| 5,575,812 A | 11/1996 | Owens |

(Continued)

FOREIGN PATENT DOCUMENTS

| EP | 0672400 | 9/1995 | |
| WO | WO 2013093917 A1 * | 6/2013 | ............. A61F 7/106 |

*Primary Examiner* — Kaitlyn E Smith
*Assistant Examiner* — Christine A Dedoulis
(74) *Attorney, Agent, or Firm* — Dykema Gossett PLLC

(57) ABSTRACT

Disclosed is a device for cooling a body or body part for medical or performance-enhancing purposes, said device consisting of one or more cooling elements (11), said cooling element (11) being provided with a cover (1) that is filled with meltable cooling solid (2). The disclosed device is characterized in that an additional apparatus for displacing the already melted portion (8) of the cooling solid (2) from the contact surface (7) to the body is provided inside the cover (1), the expandable member (4, 6) being preferably designed in the form of a filled member (4) of a spring element (6) or of a foamed article. Also disclosed is an additional device which is characterized in that a layer (16) of thermochromic material indicates when a threshold temperature is exceeded, said layer (16) being applied to the bottom side of the expandable member and thus being pressed against the remaining solid portion of the cooling solid, the cover (1) being transparent in this case.

4 Claims, 2 Drawing Sheets

(52) U.S. Cl.
CPC . *A61F 2007/0095* (2013.01); *A61F 2007/108* (2013.01); *F25D 2303/0822* (2013.01); *F25D 2331/8014* (2013.01)

(58) Field of Classification Search
USPC .......................................................... 607/114
See application file for complete search history.

(56) References Cited

U.S. PATENT DOCUMENTS

| | | | |
|---|---|---|---|
| 5,897,582 | A | 4/1999 | Agnatovech et al. |
| 7,824,436 | B2 | 11/2010 | Barbut et al. |
| 2002/0035745 | A1 | 3/2002 | Spell |
| 2008/0027523 | A1* | 1/2008 | Behringer ................. A61F 7/10 607/109 |
| 2009/0036960 | A1 | 2/2009 | Blair |
| 2009/0149772 | A1* | 6/2009 | MacDonald ........... A61Q 19/00 600/549 |
| 2010/0211143 | A1 | 8/2010 | Lu |
| 2013/0261712 | A1* | 10/2013 | Ebel ......................... A61F 7/02 607/112 |
| 2015/0114858 | A1 | 4/2015 | Rothenberg |

* cited by examiner

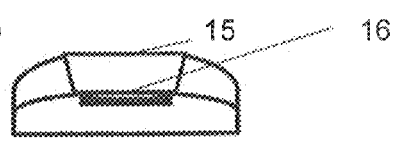
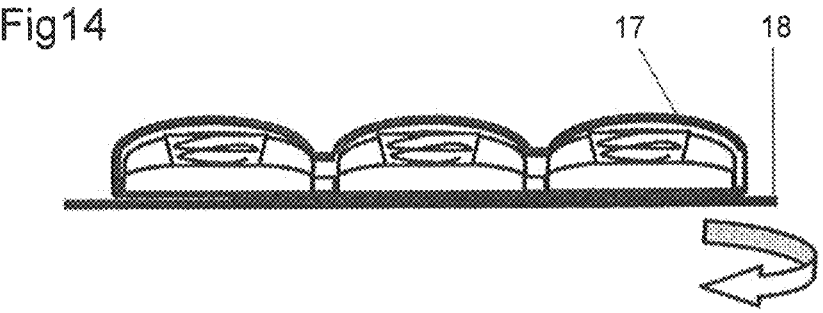

COOLING MAT COMPRISING EXPANDABLE ELEMENTS FOR COOLING A BODY OR BODY PART FOR MEDICAL OR PERFORMANCE-ENHANCING PURPOSES (COOL APP)

BACKGROUND OF THE INVENTION

The invention relates to an apparatus for cooling a body or a body part by means of a heat-extracting cover. Such apparatuses are preferably used for the temperature management of humans or animals which require cooling of the body core temperature to beneath 36° C. (therapeutic hypothermia) during or after cardiac arrest, myocardial infarction, stroke, septic shock, apoplexy, injuries to the spine or traumatic brain injury.

Even after successful revival after cardiac arrest, the long-term chances and quality of survival are frequently very low. Approximately 55% of the patients die even after successful reanimation from long-term effects of cardiac arrest within 12 months. A major part of the surviving patients is subject to serious damage of the brain and the nervous system, thus massively impairing the quality of life. The damage not only occurs during cardiac arrest but also progresses even after successful revival. This damage is known as post-reanimation syndrome. Surveys have shown that the chances of survival and the quality of survival of patients with cardiac arrest can be improved considerably after successful revival by rapidly lowering the body temperature to approximately 33° C. for the duration of 24 to 48 hours. As a result of this cooling, which is known in the medical field as therapeutic hypothermia, not only the oxygen consumption in the brain of the patient is reduced but also various cellular degradation processes are suppressed or slowed down. The endogenous repair processes are thus given the necessary time. As a result, the probability of survival and the quality of survival rise significantly. Further fields of application of such an efficiently cooling cover can be found in the area of orthopaedics, dental medicine and in cases where swelling is to be avoided after an injury or in the post-operative field.

Studies have shown that an application in patients after a stroke can also promote the recovery process. The application of cold is also provided in rheumatic phenomena and other inflammatory processes.

According to a study of the University of Münster, the application of cooling on humans before or during sports can also be applied for increasing performance.

Currently available, non-invasive cooling apparatuses usually require cooling units for preparing the cooling energy, which generate the cold during the cooling mostly from electrical power and distribute the cold medium in a liquid or gaseous manner over the entire body or parts of the body for extracting the energy via mats or sprinkling units. Invasive methods also require high quantities of energy during or before the application, which is provided by mostly converting electrical power in cooling units.

a semi-invasive cooling system wherein a highly volatile gas, especially perfluorocarbon, is injected into the nasal cavity. As a result of the cooling by evaporation which occurs during the expansion of the gas, energy is extracted from the nasal mucosa and the bloodstream is thus cooled. There is a high risk of frostbite in the face however as a result of the direct action of the gas on the vessels and the nasal mucosa.

Known cooling apparatuses without an external apparatus for through-flow with liquid or gas are formed as cooling mats. Individual parts of a cooling mat which are used for storing energy are designated below as cooling solids. The cooling solids are filled with a cold liquid, gel or ice, and provided with adhesive films, belts or Velcro tapes in order to ensure good contact and thus good heat transfer between the cooling solid and the patients to be cooled. The respective boundary layer of the cooling solid is heated during heating of the individual cooling solids. As a result, the cooling performance considerably decreases over time as a result of the decreasing heat transfer, even if sufficient cooling capacity would be available in the cooling solid itself. Since water for example has a low thermal conductivity of 0.597 W/(m·K) (at 20° C.), the heat transfer between the solid portion of an ice-like cooling solid and the surface of the patient rapidly decreases by the liquid barrier occurring at the boundary layer and thus becomes inefficient.

U.S. Patent Publication 2010211143 A1 describes an apparatus for pressing cooling solids by means of overlapping pressure chambers which comprises a unit for pressure adjustment. This unit and all known apparatuses show the common disadvantage that the cooling solid is pressed in its entirety against the surface to be cooled, but the formation of an insulating layer as described above cannot be prevented. U.S. Patent Publication 2009036960 describes a casing made of ice whose liquid portion is absorbed by polymer crystals during melting. The disadvantage of this apparatus is that even if an insulating layer is thus removed by gravity, the filling of the cover already needs to occur with frozen material because otherwise the introduced liquid is absorbed immediately by the polymer crystals. Such an apparatus is therefore unsuitable for medical use in the clinical field because the filling of a cover with ice is very laborious and an even only temporary heating destroys the apparatus. It is a further disadvantage of this apparatus that the ice needs to be introduced in a crushed form in order to enable flexibility for adjustment to the shape of the body. As a result, the cooling solid is thus inevitably provided with a major air component, which on its part reduces the efficiency of cooling by insulation. It is a further disadvantage of the apparatus described in this patent that the discharge of the liquid layer depends on the position and does not occur independently of the direction of gravity. As a result, this apparatus is not suitable for full-body cooling in which the arrangement of the cooling solid in relation to the collecting apparatus for the liquid should be arbitrary.

The patent AT 414 094 B describes a cover which is cooled beneath the freezing point prior to application. and the released melting energy is used during cooling for the rapid cooling of the patient. An improvement of the conductivity of the liquid is achieved by introducing heat-conductive materials for preventing the reduction in the thermal conduction between the patient and the still solid cooling solid by the molten liquid. The introduction of these materials is complex from a production standpoint and materials such as graphite lead to high levels of soiling in the case of an escape of the liquid from the cooling solid as a result of damage to the cover. In addition to the irritation of the medical staff by the strong colouring effect of the used material of graphite, there is also the risk of influencing the electrical conductivity during the escape of the material and thus influencing medical instruments such as the ECG. These additions or supplements also increase the specific weight relating to the cooling power.

It is a further relevant property of cooling mats to indicate the respective temperature of the cooling mat. The treating medical staff or the other user is thus informed that the cooling mat still cools to a sufficient extent or needs to be exchanged. Conventional cooling mats usually comprise the indicators in form of thermochromic inks that are positioned on the surface. The temperature differences within the cooling solid itself are very high, especially in cooling solids which utilise the melt energy for cooling. Boundary layers can already reach room or body temperature, although sufficient melt energy is still present in the solid portions. A positioning of the temperature indicator on the surface of a cooling or heating body or at an undefined position in the liquid-ice mixture therefore leads to a premature or late removal and exchange of the cooling mats, depending on the respective situation. Since cooling mats cause high costs for medical applications, a more precise indication of the temperature can offer substantial possibilities for savings and improved security for the patient.

U.S. Patent 5575812 describes a cooling or heating mat, comprising a temperature indicator positioned on the outer skin of the cooling solid on the surface in form of writing consisting of thermochromic inks. This type of temperature indication on the surface is mostly sufficiently precise for gel-like or liquid cooling solids of smaller extension. For cooling solids with a higher storage capacity, which also utilise the melt energy, it is highly imprecise. The temperature indicated by the indicator can deviate from the temperature of the still solid portion of the cooling solid by up to 10° in each direction. As a result, a cooling element removed from the freezer can signal a temperature range on the surface which is still secure for cooling, although the side facing the patient still has a skin-damaging temperature. This erroneous indication can lead to serious injuries of the patient who is usually unconscious and therefore insensitive to pain during the therapy. On the other hand, the temperature indicated by the thermal indicator attached to the surface can already signal room temperature and thus inefficiency for the purposes of cooling, while the solid portions facing the patient still allow active cooling. A premature exchange of the cooling mat represents a serious disadvantage, both with respect to the workload of the medical staff and also with respect to the costs of an additional cooling mat.

The invention is therefore based on the object, on the basis of the prior art, to provide a mat for cooling at least parts of the body of humans and animals with which high cooling rates can be achieved in a simple, environmentally compatible and efficient manner. The cooling system shall be as small and light as possible and shall be ready for operation during application without any external energy source so that the application is also enabled in a mobile manner. Furthermore, the cooling mat shall operate without any addition of materials for increasing the thermal conductivity in order to overcome the aforementioned disadvantages. Temperature indication shall indicate the temperature of the remaining solid portion of a cooling solid. at the boundary surface between the patient and the cooling solid in a reliable manner and with high precision. The illustrated disadvantages of known systems shall be avoided or reduced.

SUMMARY OF THE INVENTION

The objects in accordance with the invention are achieved by the for temperature control of at least parts of the body of humans or animals whenever this is required for medical, therapeutic, performance-enhancing or comfort-improving purposes. Cooling occurs with cooling solids in form of a meltable material such as water, which is introduced into a cooling mat consisting of preferably small, air-free individual cells still in liquid form and is frozen in a freezer preferably at temperatures of approximately −6° C., The cooling mat is applied to the body or body part for application by means of an adhesive layer or a mechanical apparatus. The melt energy becomes effective for the cooling process. If this cooling mat is brought into connection with the body or body part to be cooled, the cooling solid begins to melt. Without a special apparatus the cooling power would decrease considerably after a few minutes because a liquid layer is produced between the body and the still solid part in the cooling mat, which liquid layer forms a thermal insulator as a result of the adverse thermal conductivity of most liquids or of water. The energy can thus only be transmitted very slowly at the contact surface and the desired rapid cooling of the body and thus the patient does not occur. The "negative" energy stored in the cooling solid as an energy sink would then extract the energy required for the melting process from the ambient environment.

The apparatus in accordance with the invention for cooling a body or a body part for medical or performance-enhancing purposes by means of a mat which extracts heat from a cooling mass by means of melt heat is characterized in that the already melted portion of the cooling mass between the still solid portion of the cooling mass and the contact surface to the body or body part is continuously removed in an active manner, irrespective of the position. The cooling of a body with 80 kg by approximately 3° C. by assuming 70% efficiency of the total system for cooling can occur with 3.6 kg of ice at a melt heat of the water of 0.334 MJ/kg and a specific thermal capacity of the human of 0.035 MJ/kg. The reduction in the temperature by 3° C. is recommended in therapeutic hypothermia.

In order to maintain good thermal conductivity between the solid cooling solid and the skin surface during the entire melting process, an apparatus for the selective pressing of the still solid portion of a cooling solid against a body part to be cooled and for displacing the liquid portions on the boundary layer to the body parts to be cooled is characterized in accordance with the invention in that in a preferably cuboid cooling unit a preferably centrally positioned expandable element applies a directed pressure onto the still solid portion of the cooling solid. In order to enable good adjustment of the cooling solids connected to the cooling mat to the surface of the body and to avoid breakage of the solid portions within an individual cooling solid, the individual cooling solids are preferably formed in a size of approximately 30×30 mm base surface. The cooling mat is stored in a dimensionally stable outer cover during freezing, which is preferably also used as a packaging. If the water or the other cooling liquid expands during freezing, the expandable elements in accordance with the invention are compressed. If the cooling mat is applied to the body part by gluing or other mechanical apparatuses, the solid cooling solid melts. The thus occurring liquid is displaced from the contact surface between the solid portion of the cooling solid and the body part to be cooled by the pressure which is exerted by the compressed expandable elements on the still solid portion of the cooling solid. As a result, the cooling power can be kept substantially constant during the entire melting process. The expandable element can be formed both in a gaseous and also as a solid body in form of paraffins for example.

A further embodiment of the apparatus for removing the insulating liquid layer consists of using an expandable element in form of a small spring element or a permanently elastic material such as foam in an expandable body. The expandable body is configured and arranged to be gas-filled.

The exterior cover of the cooling solid and the expandable element situated above said cooling solid is preferably made of thermoplastic material, thus fulfilling both the tensile strength and processing capability as well as the requirements placed on the tightness and biocompatibility of the material.

In contrast to conventional temperature indicators, the apparatus for temperature indication on the basis of thermochromic inks is positioned in the interior of the cooling solid, on the bottom side of the expandable element in accordance with the invention. The expandable element is formed from a transparent film if a temperature indicator is used, thus allowing transparency through the expandable body. The attachment in this region in connection with the utilisation of an expandable element allows precise determination of a threshold temperature of the still solid cooling solid in contrast to conventional temperature indicators, which threshold temperature substantially coincides with the temperature of the boundary layer to the body. The user is thus enabled, even during the treatment, to recognise easily whether the cooling mat still supplies sufficient cooling power or needs to be exchanged. This apparatus for the display of the temperature threshold value allows considerable cost savings and increased security for the patient.

BRIEF DESCRIPTION OF THE DRAWINGS

The present invention is now explained in greater detail by reference to embodiments shown in the enclosed drawings, wherein:

FIG. 2 shows a cooling element with a gaseous or solid expandable element 4 which is integrated in accordance with the invention in the cooling element 1 and is surrounded by an elastic film 3. FIG. 3 shows a mechanical apparatus in accordance with the invention in form of a spring or another elastic material 6 in a gas-filled body, which is also separated by an elastic cover 5 from the cooling solid 1.

FIG. 7 shows that a liquid layer 8 is formed in cooling elements which do not comprise any apparatus in accordance with the invention and which significantly reduce the heat transmission between the solid cooling solid 2 and the skin surface 7 already after a short period of time.

FIGS. 8 and 9 show two embodiments of the apparatus in accordance with the invention. FIG. 8 shows that after the heating of the cooling solid the still solid portion of the cooling solid 2 is pressed against the skin, as a result of the expansion of the expandable element 4 and the already melted liquid 8 is thus displaced in the upward direction. FIG. 9 shows an expansion of the mechanical expandable element 6, which exerts a selective and purposeful pressure on the still solid portion of the cooling solid 2 and displaces the already melted portion 8 of the cooling solid to the side facing away from the skin surface 7. As a result, the direct contact of the still solid portion of the cooling solid to the skin surface and thus the thermal conduction and efficiency of the cooling mat can thus be maintained.

FIG. 13 shows a sectional view of the positioning of a thermochromic in layer 16, which allows a precise indication of the temperature of the cooling mat in the interior. The attachment in accordance with the invention to the bottom side of the expandable element ensures contact with the still solid portion of the cooling solid on a long-term basis, as a result of which the reaching of a temperature threshold value which signals the decrease in the efficiency can be indicated in a highly precise manner by colour indicators. When using a transparent cover of the expandable element, this limit value can be determined from the outside by the thus provided inspection window 15.

FIG. 14 shows a dimensionally-stable outer cover 17, in which the cooling mat is stored during the freezing process for avoiding uncontrolled expansion. This outer cover can simultaneously be used as a packaging. The bottom layer 18 can be removed as in a blister packaging for removing the cooling mat.

Figure 1:
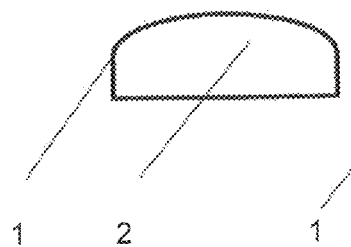
FIGS. 1, 2 and 3 each show a schematic sectional view through an element of a cooling mat. Each of these elements is formed by a cover 1 and a cooling solid 2, which consists of a liquid, preferably water. The liquid shall transfer to the solid state at a temperature of approximately +10° C. to −10° C. The elements are subsequently referred to below as cooling elements. The cooling element of FIG. 1 is shown without the apparatus in accordance with the invention and only contains the cooling solid 2.
Figure 2:
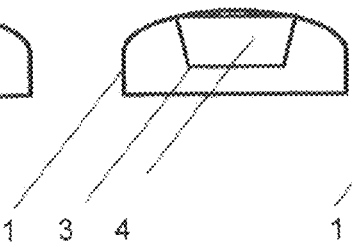
Figure 3:
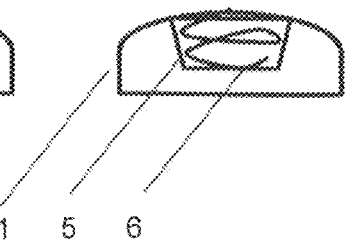
Figure 4:
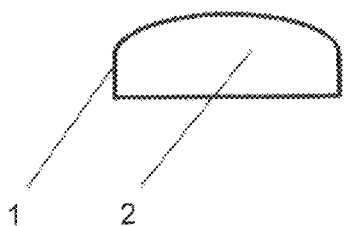
FIGS. 4, 5 and 6 show the cooling elements of FIGS. 1, 2 and 3 in the frozen state. The cover 1 is so elastic in all cases that it can absorb the expansion of the cooling solid 2 during freezing without tearing, but produces a tension which compresses the expandable element 4 in FIG. 5 or the elastic material such as a spring 6 in the gas-filled body in FIG. 6. The covers of the expandable element in FIGS. 5 and 6 are more elastic than the cover 1.
Figure 5:
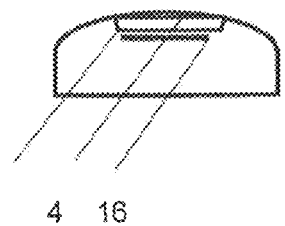
Figure 6:
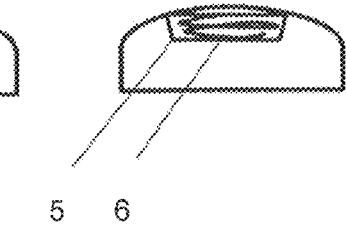
Figure 7:
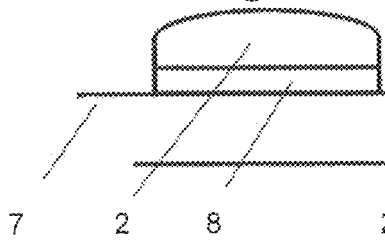
FIGS. 7, 8 and 9 show the cooling elements of FIGS. 1 to 3 and 4 to 6 after the application to a body or body part on the skin surface 7, which is schematically shown in a sectional view.
Figure 8:
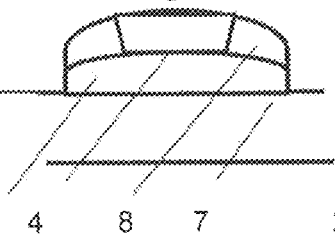
Figure 9:
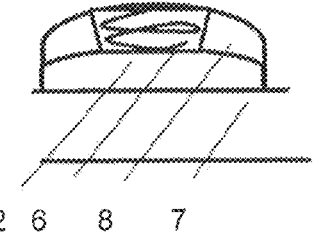
Figure 10:
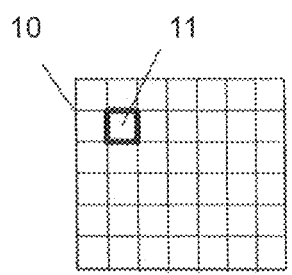
FIG. 10 shows a top view of an example how several cooling elements 11, which are provided in this case in square form, can be combined to form a cooling mat 10.
Figure 11:
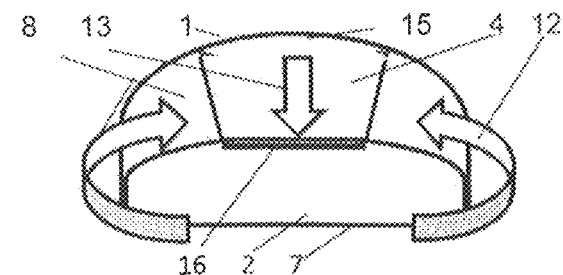
FIG. 11 shows the forces in a cooling solid during the melting process. The arrow 13 symbolises the force which presses the still solid portion of the cooling solid, against the opposite wall and thus displaces the already liquid portion of the cooling solid on the contact surface to the skin 7 in the upward direction according to the arrows 12.
Figure 12:
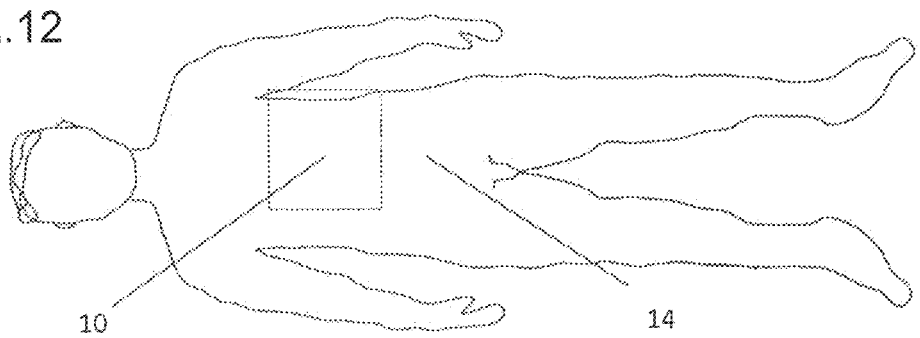
FIG. 12 shows a positioning example how the cooling mat 10 can be applied to a body or body part 14 by means of an adhesive film or by mechanical apparatuses such as bandages.

The invention claimed is:

1. An apparatus for cooling a body or body part for medical or performance-enhancing purposes, the apparatus comprising:
   a contact surface configured and arranged to contact the body or body part;
   a cooling element which includes
      an elastic cover configured and arranged to enclose a meltable cooling solid,
      a device configured and arranged to displace melted cooling solid of the meltable cooling solid away from the contact surface, the device including an expandable body having a spring element, the expandable body configured and arranged to be gas-filled; and
   a dimensionally-stable outer cover configured and arranged to
      enclose the cooling element,
      prevent uncontrolled expansion of the cooling element when subjected to a freezing temperature, and
      store the cooling element during freezing and which is removable before applying the cooling element on the body or body part.

2. The apparatus according to claim 1, wherein the cover is transparent, and including a layer of thermochromic material on a bottom side of the expandable body to be pressed against a frozen portion of the cooling solid to indicate temperatures exceeding a predetermined threshold.

3. The apparatus according to claim 1, further including an adhesive layer configured and arranged for application to the body or body part.

4. The apparatus according to claim 1, wherein the meltable cooling solid is water.

\* \* \* \* \*